US011712008B2

(12) United States Patent
Coleman et al.

(10) Patent No.: US 11,712,008 B2
(45) Date of Patent: Aug. 1, 2023

(54) LOCALIZED DATA MAPPING FOR INDOOR AND OUTDOOR APPLICATIONS

(71) Applicant: MTD Products Inc, Valley City, OH (US)

(72) Inventors: John Coleman, Sheffield (GB); Peter Hoffman, Avon, OH (US)

(73) Assignee: MTD PRODUCTS INC, Valley City, OH (US)

( * ) Notice: Subject to any disclaimer, the term of this patent is extended or adjusted under 35 U.S.C. 154(b) by 714 days.

(21) Appl. No.: 16/583,621

(22) Filed: Sep. 26, 2019

(65) Prior Publication Data

US 2020/0113142 A1 Apr. 16, 2020

Related U.S. Application Data

(60) Provisional application No. 62/744,174, filed on Oct. 11, 2018.

(51) Int. Cl.
*A01G 20/30* (2018.01)
*G06F 16/29* (2019.01)
(Continued)

(52) U.S. Cl.
CPC ............ *A01G 20/30* (2018.02); *A01C 21/007* (2013.01); *A01D 43/00* (2013.01); *A01G 25/16* (2013.01);
(Continued)

(58) Field of Classification Search
CPC .................................................. A01G 20/30
See application file for complete search history.

(56) References Cited

U.S. PATENT DOCUMENTS 7,103,451 B2 * 9/2006 Seal ..................... A01B 79/005
382/110
7,362,439 B2 * 4/2008 Franzen ............... A01D 34/006
382/106
(Continued)

FOREIGN PATENT DOCUMENTS

DE 4342171 A1 5/1994
EP 0761084 A1 3/1997
(Continued)

OTHER PUBLICATIONS

International Search Report and Written Opinion issued in International Application No. PCT/US2019/053163 dated Apr. 6, 2020; 18 pages.
(Continued)

*Primary Examiner* — Michael A Berns
(74) *Attorney, Agent, or Firm* — Wegman Hessler (57) ABSTRACT

A method for generating a localized data map, the method including (a) traversing an area with a machine, the machine including at least one sensor, wherein the sensor is configured to receive data; (b) collecting data of the area utilizing the sensor; and (c) communicating the data to generate a localized data map. A system and method for generating a localized turf grass data map, the method including (a) traversing an area of turf grass with an outdoor power equipment machine, the outdoor power equipment machine including at least one sensor, wherein the sensor is configured to receive data; (b) collecting turf grass data utilizing the sensor; and (c) communicating the turf grass data to generate a localized turf grass data map.

12 Claims, 7 Drawing Sheets

(51) Int. Cl.

| | | |
|---|---|---|
| *A01C 21/00* | (2006.01) | |
| *A01D 43/00* | (2006.01) | |
| *A01G 25/16* | (2006.01) | |
| *A01M 21/00* | (2006.01) | |
| *G01C 15/00* | (2006.01) | |
| *G01L 3/00* | (2006.01) | |
| *G01M 15/04* | (2006.01) | |
| *G01N 33/00* | (2006.01) | |
| *A01D 101/00* | (2006.01) | |

(52) U.S. Cl.
 CPC ............ *A01M 21/00* (2013.01); *G01C 15/00* (2013.01); *G01L 3/00* (2013.01); *G01M 15/04* (2013.01); *G01N 33/0098* (2013.01); *G06F 16/29* (2019.01); *A01D 2101/00* (2013.01)

(56) References Cited

U.S. PATENT DOCUMENTS

| | | | |
|---|---|---|---|
| 8,285,460 B2* | 10/2012 | Hoffman | A01B 79/005 239/DIG. 15 |
| 8,849,523 B1 | 9/2014 | Chan et al. | |
| 9,200,985 B2* | 12/2015 | Rice | G01M 99/008 |
| 9,511,633 B2* | 12/2016 | Anderson | A01B 69/007 |
| 10,034,421 B2* | 7/2018 | Doughty | G05D 1/0044 |
| 10,690,504 B2* | 6/2020 | Szubbocsev | G06V 40/103 |
| 11,282,225 B2* | 3/2022 | Klimovich | G01C 21/30 |
| 2005/0024213 A1 | 2/2005 | Franzen et al. | |
| 2005/0149235 A1 | 7/2005 | Seal et al. | |
| 2013/0046419 A1 | 2/2013 | Anderson | |
| 2013/0191073 A1 | 7/2013 | Rice et al. | |
| 2017/0020064 A1 | 1/2017 | Doughty et al. | |
| 2018/0143130 A1* | 5/2018 | Shearer | A01G 7/00 |
| 2020/0113142 A1* | 4/2020 | Coleman | G01L 3/00 |
| 2021/0337716 A1* | 11/2021 | Lee | B60W 60/0025 |

FOREIGN PATENT DOCUMENTS

| | | |
|---|---|---|
| EP | 0917816 A1 | 5/1999 |
| JP | 2016073252 A | 5/2016 |
| WO | 2016103068 A1 | 6/2016 |

OTHER PUBLICATIONS

Office Action for Chinese Patent Application No. 201980067221.1, dated Apr. 28, 2023, 8 pages.

\* cited by examiner

LOCALIZED DATA MAPPING FOR INDOOR AND OUTDOOR APPLICATIONS

CROSS REFERENCE TO RELATED APPLICATIONS

This application claims the priority filing benefit of U.S. Provisional Patent Application Ser. No. 62/744,174 filed Oct. 11, 2018, the entirety of which is incorporated herein by reference.

FIELD OF THE INVENTION

The disclosed systems and methods are generally directed to data mapping for various indoor and outdoor applications. The disclosed system and method relates to generating a localized data map, and more specifically, the disclosed system and method relates to a localized turf grass data map used to identify localized characteristics of areas of turf grass for the maintenance of athletic fields, sports fields and other grass covered areas.

BACKGROUND OF THE INVENTION

Sports and athletic field grasses must have dense, thick sod to be able to withstand impact, and to have the ability to recover quickly. These natural grass fields are maintained at the highest level to keep productivity at its best. Fertilization, irrigation and mowing are performed on a scheduled basis. Conventionally, the maintenance of athletic field turf grass is provided by turf maintenance crews in order to encourage grass growth during recovery periods. However, this process is time consuming and can produce uneven results where some areas of the grass covered field receive more or less treatment or attention than necessary, or may produce inaccurate results due to human error.

A field of turf grass does not generally grow, or recover from damage, at a uniform rate, and typically includes areas that grow faster/slower than other areas due to a number of factors including microclimates, e.g. amount of sunlight, shade, moisture, etc., or include areas of different turf qualities or conditions. For example, growth and recovery of the grass is delayed in areas that remain in the shade for long periods of time, and growth can be accelerated in areas exposed to more sunlight.

BRIEF SUMMARY OF THE INVENTION

Generally described hereinafter is a system and method for generating a localized turf grass data map. According to one aspect of the present system and method, the method comprises (a) traversing an area of turf grass with an outdoor power equipment machine, the outdoor power equipment machine including at least one sensor, wherein the sensor is configured to receive data; (b) collecting turf grass data utilizing the sensor; and (c) communicating the turf grass data to generate a localized turf grass data map.

In an embodiment, the step of traversing an area and the step of collecting turf grass data are simultaneous. In an embodiment, the turf grass data is associated with a measurement of at least one of (i) resistance, (ii) load, (iii) axle torque, or a combination thereof. In other embodiments, the turf grass data is associated with a measurement of at least one of (i) light, (ii) moisture content, (iii) temperature, (iv) weed presence, (v) grain, or (vi) soil compaction.

In an embodiment, the turf grass data is obtained by a sensor operatively connected to a mower blade associated with the outdoor power equipment machine. In other embodiments, the turf grass data is obtained by a sensor operatively connected to an axle of the outdoor power equipment machine. In other embodiments, the turf grass data is obtained by a sensor operatively connected to a motor associated with the outdoor power equipment machine.

In an embodiment, the step of communicating data is concurrent with or subsequent to the step of collecting turf grass data.

In an embodiment, the turf grass data map characterizes areas of high turf grass density and low turf grass density. In other embodiments, the turf grass data map is used to determine at least one turf grass demand, and wherein the turf grass demand comprises irrigation, fertilization, aeration, light, weed control, weed removal, grooming, brushing, or a combination thereof.

According to yet another aspect of the disclosed system and method, a non-transitory machine-readable medium comprising instructions stored therein, which when executed by a machine causes the machine to perform operations, is provided. The non-transitory machine-readable medium comprises (a) receiving location data associated with an area of turf grass; (b) receiving turf grass data obtained from traversing the area of turf grass with a mower; (c) aligning the location data with the turf grass data; and (d) generating a localized turf grass data map based on the location data and the turf grass data, wherein the turf grass data map characterizes turf grass.

In an embodiment, the location data is obtained by traversing the area of turf grass with a mower. In other embodiments, the location data is derived based on a map of the work area, a planned travel route, and a pre-determined mower travel speed.

In an embodiment, the turf grass data provides turf grass characteristics within the area traversed by the mower. In other embodiments, the location data provides location information associated with the area traversed by the mower.

In an embodiment, the localized turf grass data map characterizes areas of high turf grass density and low turf grass density. In other embodiments, the localized turf grass data map is used to determine turf grass demands, such as irrigation, fertilization, aeration, light, weed control, weed removal, grooming, brushing, or a combination thereof.

According to yet another aspect of the disclosed system and method, a method for determining placement of a moveable lighting apparatus is provided. The method comprising: (a) receiving mapping data at a computing device; (b) creating a light exposure map based on the mapping data; and (c) advancing a moveable lighting apparatus to a desired area.

In an embodiment, the step of receiving mapping data and the step of creating a light exposure map are contemporaneous. In an embodiment, the light exposure map depicts areas of high turf grass density and low turf grass density at specified locations in a work area. In an embodiment, the method comprises determining a placement of the moveable lighting apparatus based on the light exposure map.

In an embodiment, the step of advancing the moveable lighting apparatus is automated, manual or is accomplished via remote control. In an embodiment, the desired area comprises at least one area of low turf grass density.

According to yet another aspect of the disclosed system and method, an outdoor power equipment machine for producing a localized turf grass data map is provided. The outdoor power equipment machine comprising: a motor operatively connected to the outdoor power equipment machine; at least one sensor configured to obtain turf grass data and location data from a work area or other operating environment; a data storage system, including a storage medium to maintain the turf grass data and the location data; and a communication system for communicating the turf grass data and the location data used to produce a localized turf grass data map.

In an embodiment, the outdoor power equipment machine further comprises at least one sensor operatively connected to the mowing blade. In an embodiment, the outdoor power equipment machine provides irrigation, fertilization, aeration, weed control, weed removal, grooming, brushing, or a combination thereof.

According to yet another aspect of the disclosed system and method, a device is provided. The device comprising: a processor; and a computer readable medium, configured to store instructions, that when executed by the processor, cause the device to perform functions comprising: receiving sensor data collected by one or more sensors of an outdoor power equipment machine indicative of turf grass data in an area traversed by the mower; receiving sensor data collected by one or more sensors of the outdoor power equipment machine indicative of a history of geographic locations within the area traversed by the outdoor power equipment machine; aligning at least a portion of the turf grass sensor data with the historical geographic location sensor data; and generating a localized turf grass data map.

In an embodiment, the function of aligning at least a portion of the turf grass sensor data with the historical geographic location sensor data comprises synchronizing the turf grass sensor data with the historical geographic location sensor data to localize the turf grass sensor data to a location of the outdoor power equipment machine.

According to yet another aspect of the disclosed system and method, the method, comprises: receiving, at a computing system from an outdoor power equipment machine, turf grass sensor data indicative of localized turf grass characteristics in a work area; storing the turf grass sensor data in a memory associated with the computing system; receiving, at a computing system from the outdoor power equipment machine, sensor data indicative of a history of geographic locations of the outdoor power equipment machine within the work area; storing the historical geographic location sensor data in a memory associated with the computing system; accessing, from the memory, the turf grass sensor data and the historical geographic location sensor data; correlating the turf grass sensor data and the historical geographic location sensor data to form aligned sensor data; and generating a localized turf grass data map based on the aligned sensor data.

In an embodiment, correlating the turf grass sensor data and the historical geographic location sensor data comprises aligning at least one timestamp associated with the turf grass sensor data with at least one timestamp associated with the historical geographic location sensor data.

In an embodiment, the method comprises: identifying areas of turf grass requiring treatment within the work area based on the localized turf grass data map; and applying a treatment to the areas of turf grass in the work area. In some embodiments, the treatment comprises providing an artificial light source, irrigation, fertilization, aeration, insect control, weed control, weed removal, grooming, brushing, grass seed, or a combination thereof.

In an embodiment, the method comprises: identifying areas of high turf grass density within the work area based on the localized turf grass data map; and scheduling a mowing operation directed to the areas of high turf grass density in the work area.

According to yet another aspect of the disclosed system and method, a method for generating a localized data map is provided. The method comprises (a) traversing an area with a machine, the machine including at least one sensor, wherein the sensor is configured to receive data; (b) collecting data of the area utilizing the sensor; and (c) communicating the data to generate a localized data map.

In some embodiments, the area is either an indoor or an outdoor area. In some embodiments, the step of traversing an area and the step of collecting data are simultaneous. In some embodiments, the data is associated with a measurement of at least one of (i) resistance, (ii) load, (iii) axle torque, or a combination thereof.

In some embodiments, the data is obtained by a sensor operatively connected to an axle of the machine. In some embodiments, the data is obtained by a sensor operatively connected to a motor associated with the machine. In some embodiments, the step of communicating data is concurrent with or subsequent to the step of collecting data. In some embodiments, the data provides characteristics with the area traversed by the machine. In some embodiments, the data provides location information associated with the area traversed by the machine.

In some embodiments, the localized data map characterizes areas of the presence or absence of an object or a substance. In some embodiments, the object or the substance is associated with at least one of (i) plants, (ii) crops, (iii) ice, (iv) snow, (v) debris, (vi) carpet, (vii) asphalt, or (viii) other particulates. In some embodiments, the localized data map is used to determine indoor or outdoor demands, such as irrigation, fertilization, weed control, weed removal, ice removal, snow removal, debris removal, dust or gravel removal, or a combination thereof.

According to yet another aspect of the disclosed system and method, a machine for producing a localized data map is provided. The machine comprises a motor operatively connected to the machine; at least one sensor configured to obtain data and location data from a work area or other operating environment; a data storage system, including a storage medium to maintain the data and the location data; and a communication system for communicating the data and the location data used to produce a localized data map.

In yet another aspect of the present disclosure, a device for generating a localized data map is provided. The device comprising a processor; and a computer readable medium, configured to store instructions, that when executed by the processor, cause the device to perform functions comprising: receiving sensor data collected by one or more sensors of a machine indicative of data of an area traversed by the machine; receiving sensor data collected by one or more sensors of the machine indicative of a history of geographic locations within the area traversed by the machine; aligning at least a portion of the sensor data with the historical geographic location sensor data; and generating a localized data map.

In some embodiments, the function of aligning at least a portion of the sensor data with the historical geographic location sensor data comprises synchronizing the sensor data with the historical geographic location sensor data to localize the sensor data to a location of the machine.

According to yet another aspect of the disclosed system and method, a method for determining localized characteristics of an area is provided. The method comprising: receiving, at a computing system from a machine, sensor data indicative of localized characteristics in an outdoor work area; storing the sensor data in a memory associated with the computing system; receiving, at a computing system from the machine, sensor data indicative of a history of geographic locations of the machine within the outdoor work area; storing the historical geographic location sensor data in a memory associated with the computing system; accessing, from the memory, the sensor data and the historical geographic location sensor data; correlating the sensor data and the historical geographic location sensor data to form aligned sensor data; and generating a localized data map based on the aligned sensor data.

In some embodiments, correlating the sensor data and the historical geographic location sensor data comprises aligning at least one timestamp associated with the sensor data with at least one timestamp associated with the historical geographic location sensor data.

In an embodiment, a method includes (a) receiving mapping data at a computing device, (b) receiving soil compaction level data at a computing device, (c) creating a soil compaction level map based on the received mapping data and the received soil compaction level data, and (d) performing an aeration operation based on the soil compaction level map.

In an embodiment, an outdoor power equipment machine for producing a localized soil compaction data map includes at least one motor operatively connected to the outdoor power equipment machine, at least one sensor configured to obtain turf soil compaction data and location data from a work area or other operating environment, a data storage system, including a storage medium to maintain the turf grass data and the location data, and a communication system for communicating the turf grass data and the location data used to produce a localized turf grass data map.

BRIEF DESCRIPTION OF SEVERAL VIEWS OF THE DRAWINGS

These and other features of the disclosed system and method, and their advantages, are illustrated specifically in embodiments of the invention now to be described, by way of example, with reference to the accompanying diagrammatic drawings, in which:

FIG. 7 is a flowchart illustrating an exemplary method in accordance with an illustrative embodiment of the disclosed system and method. It should be noted that all the drawings are diagrammatic and not drawn to scale. Relative dimensions and proportions of parts of these figures have been shown exaggerated or reduced in size for the sake of clarity and convenience in the drawings. The same reference numbers are generally used to refer to corresponding or similar features in the different embodiments. Accordingly, the drawings and description are to be regarded as illustrative in nature and not as restrictive.

DETAILED DESCRIPTION

The following terms are used throughout the description, the definitions of which are provided herein to assist in understanding various aspects of the subject disclosure.

As used herein the terms "outdoor power equipment machine", "machine", "power equipment", and "equipment" are used interchangeably and refer to most any type of mowing device, aerator, sprayer, irrigation, pest control, or most any other type of machine used to maintain an area of turf. The term "machine" may also include any machine, device, or other apparatus used for traversing outdoor spaces such as, but not limited to, a parking lot, rooftop, or rooftop garden; or alternatively, indoor spaces, such as, but not limited to, the interior of a home, a greenhouse, or other building structure.

As used herein the terms "mower" and "mowing device" are used interchangeably and refer to any of an autonomous mower, reel mower, manual mower, walk-behind mower, riding mower, commercial mower, and most any other mowing machine.

As used herein, the term "work area" refers to (1) areas of turf grass that are grown and maintained, for example, but not limited to, on athletic fields, sports fields, lawns, golf courses, baseball fields, football fields, tennis courts, soccer fields, recreational sites, roof top gardens, fields, and other similar grass covered areas, and (2) any other desired indoor or outdoor region.

As used herein, the term "turf grass" refers to numerous types and varieties of grasses such as those used on lawns, athletic fields, sports fields, and the work areas detailed above.

As used herein, the term "data" refers to and includes such data or information as (i) turf grass data, (ii) data collected within a desired indoor space, and/or (iii) data collected within a desired outdoor space. As used herein, the term "turf grass data" refers to and includes such data or information as (i) grass demands, such as mowing, irrigation, fertilization, insect control, light, and combinations thereof, (ii) turf grass density, (iii) soil compaction, (iv) moisture content, (v) presence or absence of insects, (vi) presence or absence of weeds, (vii) temperature and/or humidity, (viii) turf grain, and combinations thereof.

Figure 1:
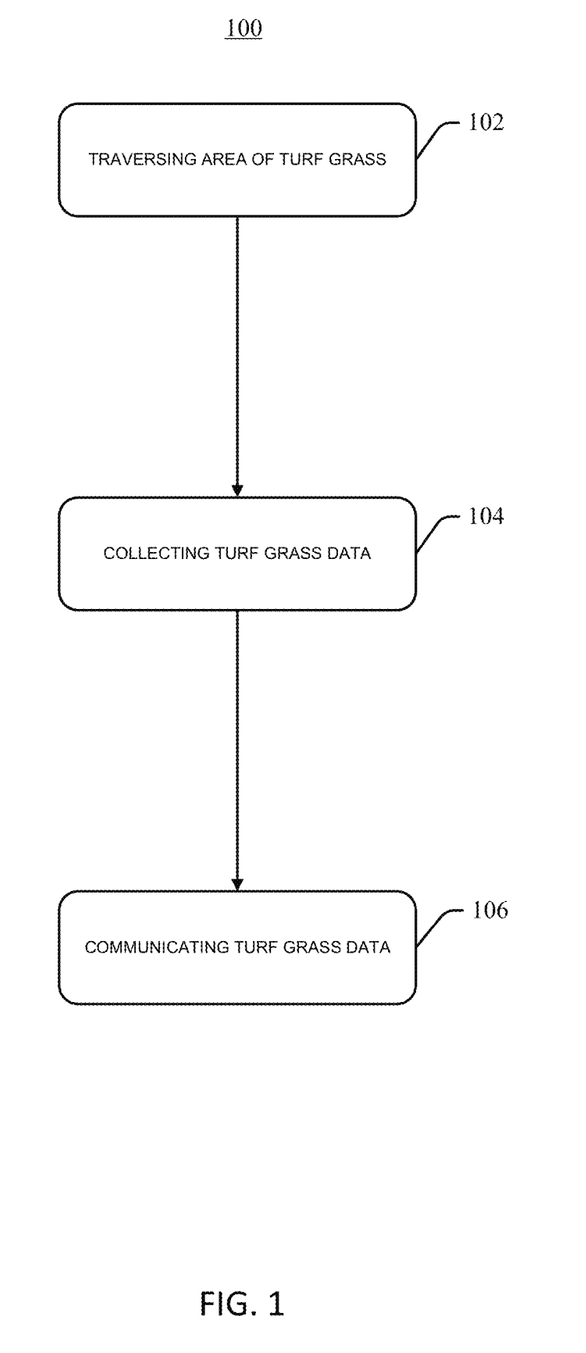
FIG. 1 is a flowchart illustrating an exemplary method in accordance with an illustrative embodiment of the disclosed system and method.

As used herein, the term "turf grass density" refers to and includes such characteristics as grass quantity, spatial density, and areas of high or low grass thickness, areas of high or low grass height, frequency, or the like. With reference to FIG. 1, a flowchart illustrating an exemplary method 100 for generating a localized turf grass data map is shown. The method 100 includes (a) traversing an area of turf grass with a mowing device (step 102), (b) collecting turf grass data from a sensor (step 104), and (c) communicating turf grass data to generate a localized turf grass data map (step 106).

While, for purposes of simplicity of explanation, the methodologies illustrated in FIGS. 1-3 and 6 are shown and described as a series of acts, it is to be understood and appreciated that the subject disclosure is not limited by the order of acts, as some acts may, in accordance with the disclosure, occur in a different order and/or concurrently with other acts from that shown and described herein. For example, those skilled in the art will understand and appreciate that a methodology could alternatively be represented as a series of interrelated states or events, such as in a state diagram. Moreover, not all illustrated acts may be required to implement a methodology in accordance with the disclosure.

In step 102, a mowing device traverses a work area. The mowing device of the disclosed system and method includes at least one sensor configured to collect data indicative of the turf grass in the work area. In some embodiments, in step 102, an outdoor power equipment machine traverses a work area, wherein the outdoor power equipment machine includes at least one sensor configured to collect data indicative of the turf grass in the work area.

In step 104, while traversing the work area, turf grass data is collected by the sensors. In an embodiment, data is gathered during operation of the outdoor power equipment machine, and no separate measures are needed to traverse the work area apart from such operation. Thus, in some embodiments, the step of traversing an area (step 102) and the step of collecting turf grass data (step 104) occur simultaneously.

In some embodiments, the turf grass data is determined by collecting or measuring (i) resistance, (ii) load, (iii) axle torque associated with the outdoor power equipment machine or mowing device, or a combination thereof. In some embodiments, the turf grass data is obtained by one or more sensors operatively connected to a mower blade of the mowing device. The sensor can be configured to collect data associated with a varying amount of resistance at the mower blade during the mowing operation. In other embodiments, the turf grass data is collected utilizing a sensor operatively connected to an axle associated with the outdoor power equipment machine. The sensor can be configured to collect data associated with a varying amount of torque at the axle during operation. In yet another embodiment, the turf grass data is collected by a sensor operatively connected to a motor associated with the outdoor power equipment machine. The sensor can be configured to collect data associated with a varying amount of load on the motor during operation.

In some embodiments, the turf grass data is associated with a measurement of at least one parameter, including but not limited to, (i) light, (ii) moisture content, (iii) temperature or humidity, (iv) presence or absence of weeds, (v) grain, or (vi) soil compaction.

In some embodiments, the sensor can be configured to collect data associated with varying amounts of light the turf grass receives at a specific time and location. In other embodiments, the sensor can be a humidity gage configured to determine the amount of water vapor present at a specific time and/or location of an area of turf grass.

In other embodiments, the sensor can be a vision sensor used to view and capture either the presence or absence of a weed or weed species. Such vision sensor information can be used to identify, locate and remove the weed species. In some embodiments, weed identification and removal occur simultaneously. In other embodiments, areas containing the presence of weeds can be identified and scheduled to be removed, either manually or by any other available means.

In other embodiments, the sensor can be a force sensor or load sensor configured to measure soil compaction, indicative of how compact the ground soil of an area of turf grass is at a specific time and location. In an embodiment, sensors associated with the tines of an aerator are utilized to measure soil compaction, for example, in pounds per square inch (PSI).

Turf grass data can be collected continuously or at predetermined intervals while traversing the work area. The sensor data can be associated with a timestamp and stored in memory for later use.

During step 106, the turf grass data that has been collected is stored in memory for later use by a computing device configured to generate a localized turf grass data map.

In some embodiments, the step of communicating data (step 106) is concurrent with the step of collecting turf grass data (step 104). In other embodiments, the step of communicating data (step 106) is subsequent to the step of collection turf grass data (step 104).

The localized turf grass data map of the disclosed system and method characterizes the area of turf grass that has been traversed. In some embodiments, the localized turf grass data map characterizes areas of high turf grass density and low turf grass density. In some embodiments, the localized turf grass data map can be used to determine turf grass demands, such as mowing, irrigation, fertilization, insect control, light, and combinations thereof.

In other embodiments, a localized data map can characterize areas of high soil compaction and low soil compaction. The localized data map can characterize a level or measure of soil compaction at a specific time and location. Soil compaction has a direct correlation to the health of the plant. Aeration is a process which involves perforating the soil with holes to allow air, water and nutrients to penetrate the soil. The main reason for aerating is to alleviate soil compaction. Core aeration is a type of lawn aeration involving a machine (a lawn aerator) with hollow tines that mechanically removes plugs or "cores" of soil, and thatch from a lawn. Core aeration reduces soil compaction, creating channels through which oxygen, water, and nutrients can penetrate into the soil.

The more compacted the soil is, the more energy is required to penetrate the soil during the aeration process. Conventional aerators operate indiscriminately, that is, the aerator tines perforate uniformly over any given area of soil, even if only a small percentage of the area requires treatment. This is not ideal, since soil compaction levels over a turf grass areas are generally not uniform. For example, golf fairways, and some sports fields, include central areas which tend to become more compacted, while the outlying areas remain less compacted.

In an embodiment, an electrically driven punch tine aerator can be utilized to obtain soil compaction data. Traditional punch tine aerators include crank shafts having connecting rods with tines attached at the ends, a force sensor or load sensor in operable communication with the individual tines, or a portion of the tines, can be utilized to gather associated with soil compaction.

In an embodiment, each aerator crank can be driven with a separate motor, the current draw of each motor can be measured, and the measurement data utilized to produce a soil compaction level map, which can then be compared against a predetermined desired compaction level.

In other embodiments, a single large motor driving multiple crank shafts is utilized, and measurement data associated with the current draw of the motor is utilized to produce a soil compaction level map.

In further embodiments, soil compaction data can be measured utilizing load cells attached to some or all of the aerator's mechanically driven crank shafts.

It is time consuming and labor intensive to treat large areas of turf. Mapping the soil compaction levels for a given sports turf enables subsequent aeration processes to be tailored specifically utilizing the collected soil compaction data. A localized soil compaction data map can be utilized to a) increase or decrease spacing of the aeration operation, increasing the spacing allows the machine to travel faster, b) increase or decrease the depth of the aeration operation, decreasing the depth allows the machine to travel faster, and/or c) increase or decrease the angle entry of the tine, to affect the level of heave, decreasing the angle entry allows the machine to travel faster. This provides a more effective method of making the overall compaction levels the same, and increasing the uniformity of the playing surface.

Figure 2:
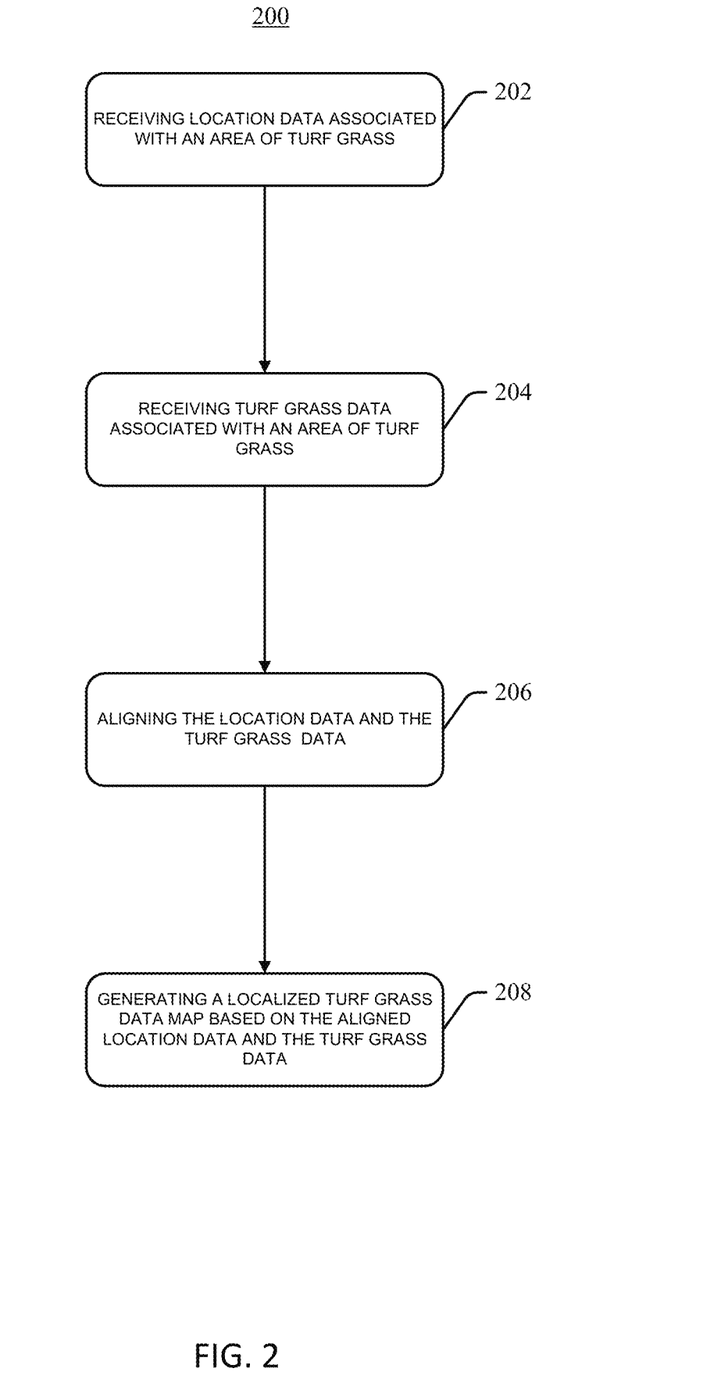
FIG. 2 is a flowchart illustrating an exemplary method in accordance with an illustrative embodiment of the disclosed system and method.

FIG. 2 illustrates a flow diagram of an example method 200 for generating a localized turf grass data map. The method 200 includes (a) receiving location data associated with an area of turf grass (step 202), (b) receiving turf grass data obtained from traversing an area of turf grass with an outdoor power equipment machine (step 204), (c) aligning the location data and the turf grass data (step 206), and (d) generating a localized turf grass data map based on the aligned location data and the turf grass data, wherein the localized turf grass data map characterizes an area of turf grass (step 208).

In step 202, location data, associated with an area of turf grass traversed with an outdoor power equipment machine, is received at a computing device 500 (e.g., a client application or server). The location data can be collected as the machine traverses the work area. The location data can be associated with a time stamp and stored in memory for later use.

The location data referred to herein includes location information associated with the area traversed by the machine. For example, location data can be obtained from real-time locating systems (RTLS), global positioning system (GPS), Light Detection and Ranging (LIDAR), ultra-wideband radar, beaconing systems, odometer, inertial measurement unit, velocity meter, acceleration sensors, Global System for Mobile Communications (GSM) localization, or most any other systems and sensors.

In other embodiments, location data can be generated on demand or can be pre-determined. For example, the location of the machine within the work area can be derived based on a map of the work area, planned travel route, and a predetermined or calculated travel speed of the machine. The location data from previous traversals of the work area can stored in memory and subsequently accessed. For example, in some embodiments, location data from previous traversals of the work area can be stored in a cloud computing environment and subsequently accessed. Location data from previous traversals of the work area can be aggregated and averaged to yield a set of reference location data. A calculated timestamp can be added to the pre-determined location data.

In step 204, turf grass data obtained from traversing an area of turf grass with an outdoor power equipment machine is received. In some embodiments, the turf grass data provides turf grass characteristics within the area traversed. The turf grass data can include, for example, numerous incremental time stamped measurements of a parameter or a combination of parameters, as measured by operation of the outdoor power equipment machine. For example, in some embodiments, the turf grass data includes multiple time stamped measurements of load on the mower motor, and/or torque as measured, for example, at an axle of the mower. In such an embodiment, sensor data associated with resistance, load, and/or torque are combined or averaged to produce the turf grass data.

In step 206, the location data and the turf grass data can be aligned, for example, by synchronizing of the timestamp information of the location data and the timestamp information of the turf grass data.

In step 208, a localized turf grass data map characterizing the turf grass at locations throughout the work area is generated based on the aligned sensor data, i.e. the aligned location data and turf grass data. In some embodiments, the turf grass map can used to determine turf grass demands, such as mowing, irrigation, fertilization, insect control, light, or a combination thereof, or characteristics, such as but not limited to, turf grass density, soil compaction, moisture content, presence or absence of insects, presence or absence of weeds, presence or absence of debris, known obstructions (i.e. trees, building/stadium geometry, etc.), temperature and/or humidity, turf grain, and combinations thereof.

In an embodiment, turf grain refers to the nap of the grass, or the grain direction of the individual grass blades, which can bend slightly in a single direction. Most commonly, such grain is associated with continually mowing in one or limited directions. In terms of a sports field, grass grain can have a significant impact on the playability of the field, for example, a golf putting surfaces or greens, baseball fields, and grass tennis courts. Data relating to the grass grain direction for an area of turf grass can be utilized to inform turf grass maintenance or grooming activities such as brushing, and/or mowing direction for subsequent mowing operations.

In an embodiment, the localized turf grass data map is used to inform the application of treatments or maintenance operations. For example, areas of high turf grass density can be scheduled to be mowed more frequently than areas of low turf grass density, or treatments such as irrigation, aeration, light, fertilizer, insect control, and/or grass seed are applied to areas as indicated by the localized turf grass data map.

Figure 3:
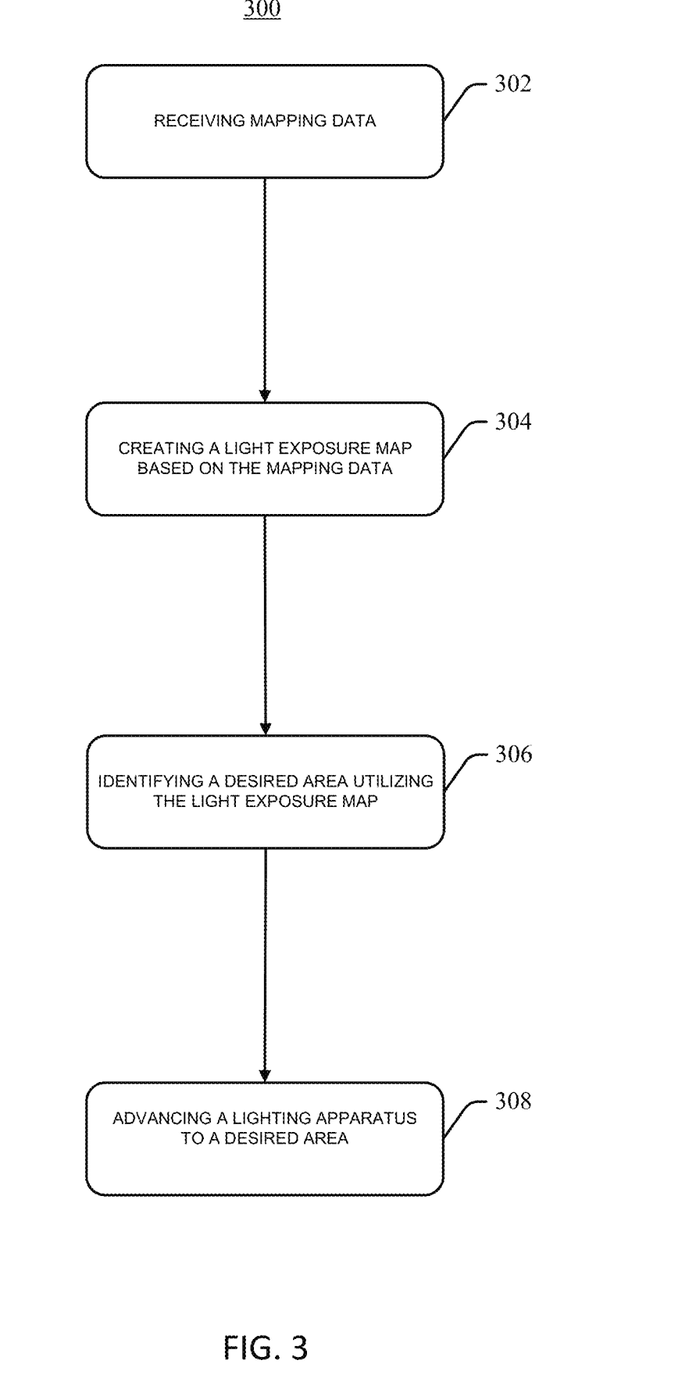
FIG. 3 is a flowchart illustrating an exemplary method in accordance with an illustrative embodiment of the disclosed system and method.

Now referring to FIG. 3, a method 300 for determining the placement of a moveable lighting apparatus is discussed. The method includes (a) receiving mapping data (step 302), (b) creating a light exposure map with the mapping data (step 304), (c) identifying a desired area utilizing the light exposure map (step 306), and (d) advancing a moveable lighting apparatus to a desired area (step 308).

In step 302, mapping data is received by a computing device 500. The mapping data can include a turf grass density map characterizing the turf grass density at locations throughout a work area.

In step 304, a light exposure map is generated utilizing the mapping data. The light exposure map indicates areas of turf grass which require additional light application or limited light.

In step 306, the light exposure map can be used to identify a desired area. For example, the appropriate placement of a moveable artificial lighting apparatus or system, which is also be referred to herein as "grow lights," can be determined. The artificial light sources or grow lights can be mounted on movable racks, and used during the day and night to stimulate growth of the grass, particularly in slower growth areas. However, such lighting systems are expensive, may not cover the entire field at once, and the amount of electricity used to power the lights is substantial. These grass lighting systems can be manually moved by an operator, who determines their placement from one area to another simply based on visual estimations and personal observations of the turf, or can be automated, based on the information received by the light exposure map. The light exposure maps in one embodiment of the disclosed system and method allow for optimal placement of the grow lights in an area of turf grass, thereby conserving resources and providing superior grass growing results when compared to traditional practices.

In some embodiments, the light exposure map depicts areas of high turf grass density and low turf grass density. Desired areas for the application of the artificial light source can be identified based on the light exposure map. For example, a user can determine proper placement of the moveable lighting apparatus. Proper placement can be visually determined based on the results and conclusions provided by the light exposure map, or can be automatically determined based on threshold values. It should be understood that the disclosed light exposure map and method of producing said light exposure map can be used in other applications, such as, but not limited to, depicting areas of high and low crop densities, as well as being used with roof top gardens in order to determine areas of high and low light exposure.

In some embodiments, the step of receiving mapping data (step 302) and the step of creating a light exposure map (step 304) are contemporaneous. In such embodiments, mapping data is received in real-time and a light exposure map is created upon receipt of such mapping data therein.

Finally, in step 308, a moveable lighting apparatus can be advanced or moved to the previously identified desired area. In some embodiments, the desired area includes areas of low turf grass density.

Additionally, the light exposure map created in step 304 can be utilized to determine optimal placement from one area to another. This is advantageous because known moveable lighting apparatuses and systems are placed simply on visual estimations and personal observations of the turf grass itself, which is neither efficient nor accurate. In some embodiments, the step of advancing the moveable lighting apparatus is automated, manual, or can be accomplished via remote control.

Figure 4:
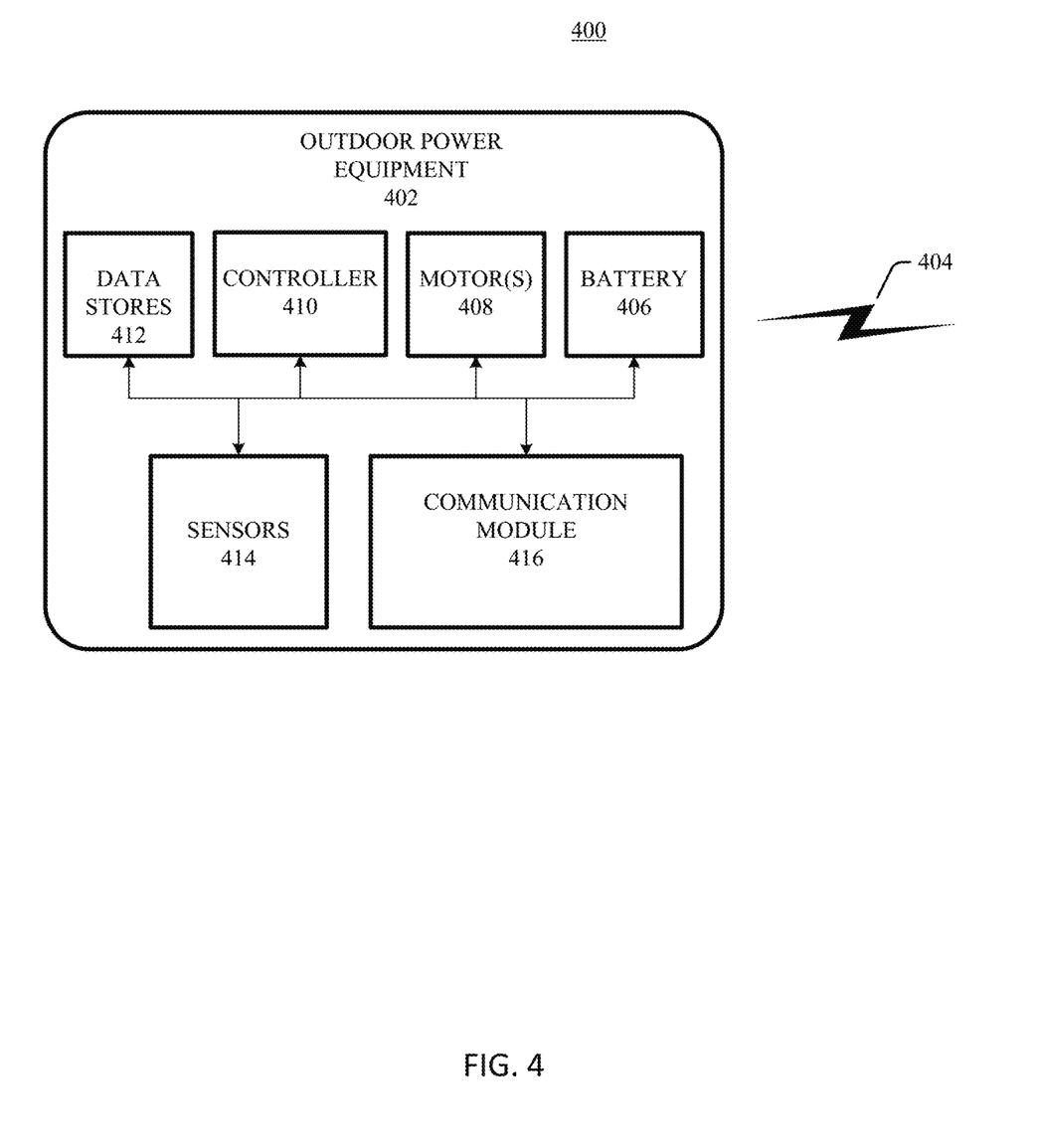
FIG. 4 is a block diagram of an outdoor power equipment machine in accordance with an illustrative embodiment of the disclosed system and method.

Many of the above-described features and applications are implemented as software processes that are specified as a set of instructions recorded on a computer readable medium. When these instructions are executed by one or more processing units (e.g., one or more processors, cores of processors, or other processing units), they cause the processing units to perform the actions indicated in the instructions. Examples of computer readable media include, but are not limited to, CD-ROMs, flash drives, random access memory (RAM), hard drives, EPROMs, etc. FIG. 4 is a block diagram of a system 400 in accordance with an illustrative embodiment of the disclosed system. An outdoor power equipment machine 402, a mower for example, communicates with a computing device 500, utilizing a communication framework 404.

The outdoor power equipment machine 402 includes a battery 406, motor 408, controller 410, data stores 412, sensors 414, and a communication module 416.

The battery 406 provides power to the outdoor power equipment machine 402 and its subsystems. The motor 408 can include, for example, an electric motor(s) or an internal combustion engine operatively connected to a mower blade (not shown). The controller 410 receives power from the battery 406 and can include most any commercially available or custom microprocessor or micro controller.

The data stores 412 comprise a storage system for storing information, for example, sensor data including location information and turf grass data can be stored and retrieved for later use. The data stores 412 can also be used to store programs local to the outdoor power equipment machine 402. The data stores 412 can include, for example, volatile solid-state memory, non-volatile solid-state memory, a magnetic storage medium, removable storage media, cloud computing device, or other suitable storage means.

Still referring to FIG. 4, the sensors 414 can be operatively connected to the outdoor power equipment machine 402 and can include most any device, hardware and/or software capable of detecting, measuring, and/or recording a property associated with the outdoor power equipment 402 and/or its environment. In an embodiment, sensors 414 can include sensors for measuring or determining location, resistance, load or torque. Sensors 414 can include real-time locating systems (RTLS), beaconing systems, odometer, inertial measurement unit, velocity meter, acceleration sensors, and other location determination sensors and systems. In an embodiment, sensors 414 can include sensors for determining light, soil compaction, moisture content, presence or absence of insects, presence or absence of weeds, presence or absence of debris, known obstructions, temperature and/or humidity, turf grain or nap, and/or combinations thereof.

The wired or wireless communication module 416 can include one or more local wireless interfaces, such as an infrared transceiver and/or an RF adapter, for example, a Bluetooth® adapter, WLAN adapter, Ultra Wideband (UWB) adapter and the like, for establishing communication with a network, an intranet, the Internet, an accessory, a mobile device, a computer, or most any other electronic device. The communication module 416 transmits and receives information related to the outdoor power equipment 402 utilizing communication framework 404.

The communication framework 404 that can be employed to facilitate communications between the outdoor power equipment 404 and the computing device 500. Communication framework 404 can include wired/wireless connectivity to a local area network (LAN) and/or larger networks, e.g., a wide area network (WAN) which can connect to a global communications network, e.g., the Internet. Communication framework 404 can provide communication utilizing, for example, cellular networks, Bluetooth®, and/or Wi-Fi technology IEEE 802.11(a, b, g, n), infrared, Ultra Wideband (UWB), or a wired connection such as a universal serial bus (USB) connection.

Figure 5:
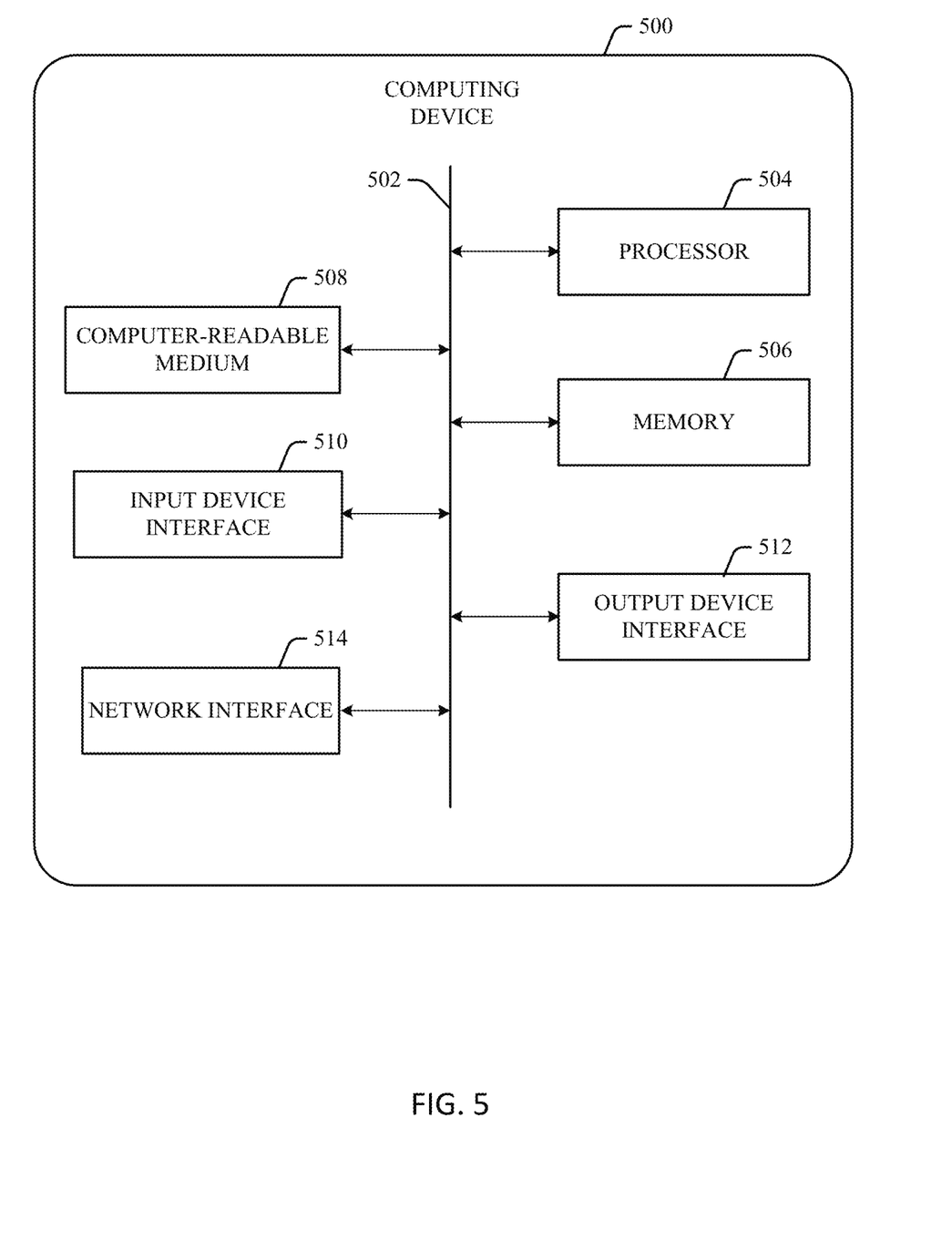
FIG. 5 is a block diagram of a computing device in accordance with an illustrative embodiment of the disclosed system and method.

FIG. 5 conceptually illustrates an electronic system with which some implementations of the subject technology are implemented. Computing system 500 can be a server, computer, phone, PDA, laptop, or tablet computer with one or more processors embedded therein or coupled thereto, or most any other sort of electronic device. Such an electronic system includes various types of computer readable media and interfaces for various other types of computer readable media.

Computing system 500 includes a bus 502 which connects the processor/processing unit(s) 504, system memory and read-only memory (ROM) 506, computer readable medium 508, also referred to herein as data stores, an input device interface 510, an output device interface 512, and a network interface 514.

In some embodiments, the processes of the subject disclosure are stored in memory 506, or the computer readable medium 508. The various memory units 506, 508 include instructions for aligning the location data and the turf grass sensor data to produce the aligned sensor data, and to generate a localized turf grass data map based on the aligned sensor data. The various memory units 506, 508 can also include instructions for creating a light exposure map, identifying a desired area utilizing the light exposure map and advancing a lighting apparatus to the desired areas. The processing units 504 retrieve instructions to execute, and data to process, from the memory units 506, 508, in order to perform the processes of some implementations.

The computer readable medium 508 is configured to store instructions. The computer readable medium 508, can be implemented as "computer readable instructions", algorithms and/or modules for execution by the processor 502. Computer readable instructions can be provided as program modules, such as functions, objects, Application Programming Interfaces (APIs), data structures, and the like, that perform particular tasks or implement particular abstract data types.

The computing device 500 can receive sensor data collected by the one or more sensors 414 of the mowing device 402 indicative of turf grass density in an area traversed by the outdoor power equipment 402. In embodiments, the device 500 can receive sensor data collected by one or more sensors 414 of the outdoor power equipment 402 that is indicative of a history of geographic locations within the work area traversed by the outdoor power equipment 402. The computing device 500 can process at least a portion of the turf grass sensor data in conjunction with the historical geographic location sensor data. In some embodiments, the device 500 can generate and output a localized turf grass data map. In some embodiments, the aforementioned functions are performed simultaneously or in succession of one another.

In some embodiments, the computing device 500 is a cloud computing device or cloud computing environment. The cloud computing environment includes the infrastructure, platforms and/or software necessary, in which a user does not need to maintain resources on a local computing device. The cloud computing environment can communicate with any type of computerized device over any type of network and/or network addressable connection (e.g., using a web browser).

Input devices used with input device interface 510 include, for example, keyboards and pointing devices. Output device interfaces 512 enables, for example, the display of images generated by the computing device 500. Output devices used with output device interface 512 include, for example, printers and display devices, such as liquid crystal displays (LCD). Devices such as a touchscreen can function as both an input and output device.

The bus 502 couples the computing device 500 to the communications network 404 through a network interface 514. The computing device 500 can be a part of a network of computers (such as a local area network ("LAN"), a wide area network ("WAN"), or an Intranet, or a network of networks, such as the Internet.

Figure 6:
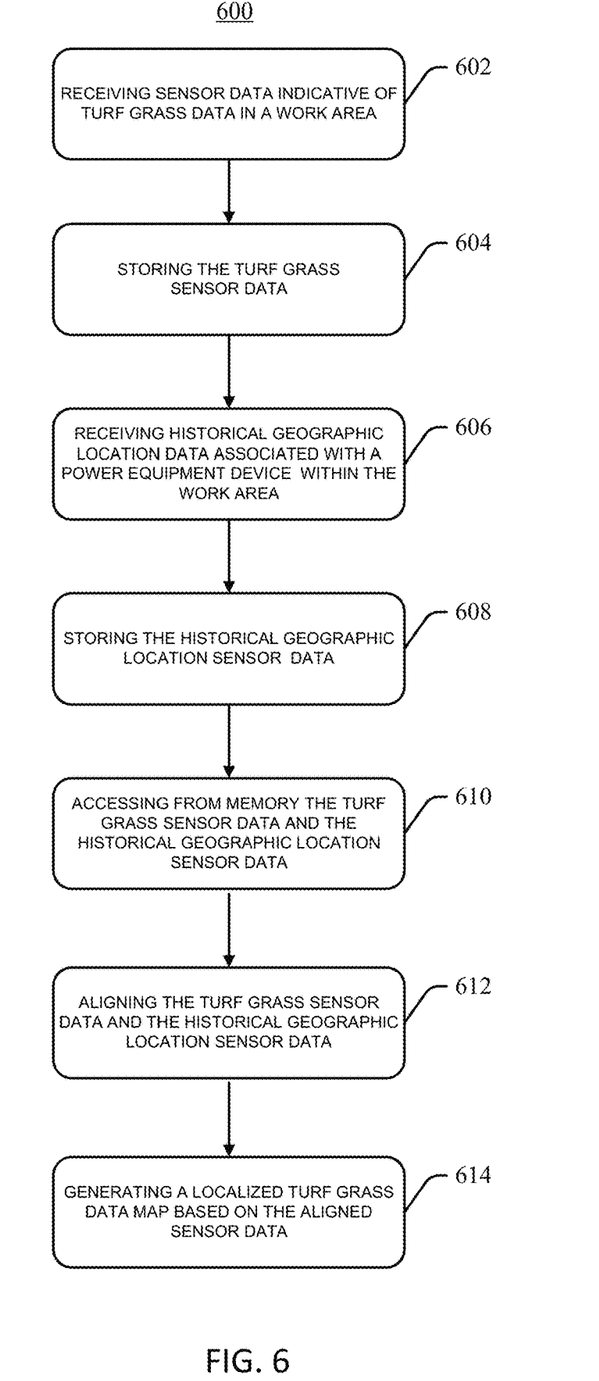
FIG. 6 is a flowchart illustrating an exemplary method in accordance with an illustrative embodiment of the disclosed system and method.

With reference to FIG. 6, a flowchart illustrating an exemplary method 600 for generating a localized turf grass data map is shown. The method 600 includes receiving sensor data indicative of turf grass data present at a location in a work area (step 602), storing the turf grass sensor data in a memory associated with the computing system 500 (step 604), receiving sensor data indicative of a history of geographic locations of the outdoor power equipment 402 within the work area (step 606), storing the historical geographic location sensor data and the turf grass sensor data in a memory associated with the computing system 500 (step 608), accessing the turf grass sensor data and the historical geographic location sensor data (step 610), aligning the turf grass sensor data and the historical geographic location sensor data to form aligned sensor data (step 612), and generating a localized turf grass data map based on the aligned sensor data (step 614).

In step 602, sensor data indicative of turf grass data present in a work area is received at a computing system 500.

In step 604, the turf grass sensor data is stored in memory associated with the computing system 500.

In step 606, sensor data indicative of a history of geographic locations of the outdoor power equipment 402 within the work area is received at a computing system 500. In some embodiments, the sensor data indicative of a history of geographic locations includes periodic automatic measurements of one or more locations of the outdoor power equipment 402 within a work area at a given time.

In step 608, the location data is stored in a memory associated with the computing system 500. In some embodiments, the memory referred to in step 608 is the same as or similar to that mentioned in step 604.

Subsequently, in step 610, the turf grass sensor data and the historical geographic location sensor data are accessed from the memory for use by a processor 504 of the computing system 500.

In step 612, the turf grass sensor data and the historical geographic location sensor data are synchronized to form aligned sensor data. In some embodiments, the aligned sensor data includes the combination of the turf grass sensor data, the historical geographic location sensor data, and non-mower collected data, such as, but not limited to, sun patterns (calendar based), local weather history, local weather predictions, length of active play or use on the turf surface, or the like. For example, in some embodiments, the aligned sensor data can be used to show sun or light patterns throughout a calendar year and be used to predictively determine where shading will most likely occur depending on the day or season, which can then be used to proactively determine turf grass demands, such as what day/season in the following year will require lighting, watering, fertilizing, etc.

In some embodiments, the function of synchronizing the turf grass sensor data and the historical geographic location sensor data includes coordinating at least one timestamp associated with the turf grass sensor data with at least one timestamp associated with the historical geographic location sensor data.

A "timestamp" shall be referred to herein as, and will be understood by one skilled in the art, the recording of numerous measured data points by a sensor or multiple sensors along a series of locations which include an indication of the time each measurement was made.

For example, the turf grass sensor data and historical geographic location sensor data can be communicated to a computing device 500. The computing device 500 is configured to receive the turf grass sensor data and the historical geographic location sensor data, synchronize the data (i.e. form aligned sensor data) according to corresponding timestamps for each data stream. The aligned sensor data can include a turf grass measurements or characteristics of turf grass at a defined or specific location within the work area.

In step 614, a localized turf grass data map based on the aligned sensor data is generated. From the aligned sensor data, a visual display or image of the data can be derived. For example, in some embodiments, the turf grass sensor data can be overlaid on the historical geographic location sensor data, such that the relative positions can be used to generate the localized turf grass data map, and specific location characteristics within the work area, such as areas of high or low turf grass density, or turf grass demands, for example, irrigation, aeration, fertilization, light, or a combination thereof, may be readily understood. In some embodiments, the turf grass data at various locations can be displayed as a dot or point, line, color, or shape, for example, on a map or an image of a sports field or other depiction of the work area.

In some embodiments, step 614 further includes identifying areas of turf grass requiring treatment within the work area based on the localized turf grass data map, and applying a treatment to the areas of turf grass in the work area. In some embodiments, the treatment includes at least one of applying an artificial light source, irrigation, fertilization, insect control, and/or grass seed. The localized turf grass data map can also be used to determine, visually or otherwise, work areas that require improvement. For example, the data map can be used to determine whether or not areas of turf grass or other areas are responding to treatments that were previously applied.

In some embodiments, the step 614 further includes identifying areas of low turf grass density within the work area based on the localized turf grass data map, and applying a treatment to the areas of low turf grass density in the work area. In some embodiments, the treatment includes at least one of applying an artificial light source, irrigation, fertilization, insect control, and/or grass seed. In other embodiments, step 614 further includes identifying areas of high turf grass density within the work area based on the turf grass density map, and scheduling a mowing operation for the areas of high turf grass density. The mowing operation can include selective mowing such that areas of high turf density are mowed and areas of low turf grass density are avoided by the mower.

In some embodiments, the step 614 includes identifying the presence of a weed or weed species and applying a treatment to such locations. Such treatments include mechanical, biological or chemical methods. In some embodiments, the chemical methods include treatments applied in spray form, or other like applications. In other embodiments, areas containing the presence of weeds can be identified and scheduled to be removed, either manually, mechanically, or by any other means available. In some embodiments, the mechanical methods can include physical removal of a weed species by a tool provided by the outdoor power equipment, or other types of like equipment or tools.

In some embodiments, the step 614 includes identifying levels of soil compaction for an area of turf grass, and applying a selective treatment to the turf grass area. Such treatments can include mechanical, biological or chemical methods. In some embodiments, the mechanical methods include an aeration process tailored specifically via, for example, collected soil compaction data, and location data to: a) increase or decrease spacing of the aeration operation, increasing the spacing allows the machine to travel faster, b) increase or decrease the depth of the aeration operation, decreasing the depth allows the machine to travel faster, and/or c) increase or decrease the angle entry of the tine, to affect the level of heave, decreasing the angle entry allows the machine to travel faster.

Figure 7:
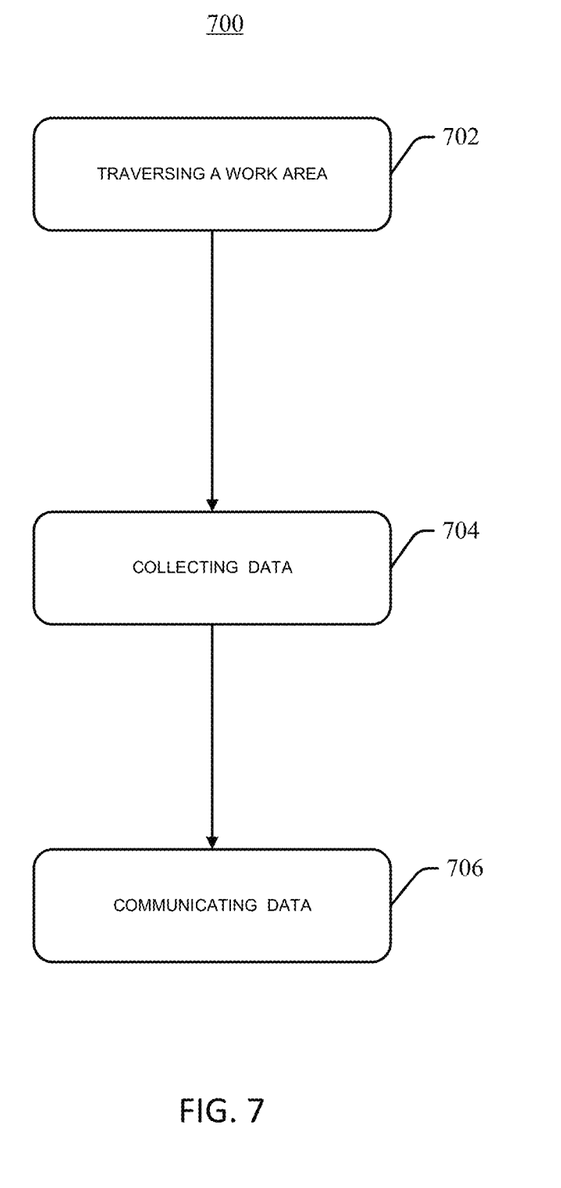

With reference to FIG. 7, a flowchart illustrating an exemplary method 700 for generating a localized data map is shown. The method 700 includes (a) traversing an area with a machine (step 702), (b) collecting data from a sensor (step 704), and (c) communicating data to generate a localized data map (step 706).

In step 702, a machine traverses a work area. The work area can include either an indoor or an outdoor area or space. In some embodiments, the indoor area can include, but is not limited to, an interior of a home, commercial building, factory, warehouse, or other like facility. In some embodiments, the outdoor area can include, but is not limited to, a parking lot, sidewalk, rooftop garden, or other rooftop space.

In step 704, data is collected from a sensor. The machine of the disclosed system includes at least one sensor configured to collect data indicative of the characteristics within a specified work area. In some embodiments, the step of traversing an area (step 702) and the step of collecting data (step 704) are simultaneous.

The data collected is associated with a measurement of at least one of (i) resistance, (ii) load, (iii) axle torque, or a combination thereof. In some embodiments, the data is obtained by a sensor operatively connected to (i) an axle of the machine, (ii) a motor of the machine, or (iii) other component associated with the machine In some embodiments, in step 704, the machine sensor is configured to collect data indicative of the presence or absence of an object or a substance located within the work area. In some embodiments, the object or the substance is associated with at least one of (i) plants, (ii) crops, (iii) ice, (iv) snow, (v) debris, (vi) carpet, (vii) asphalt, or (viii) other particulates.

In step 706, data collected from the sensor is communicated to the data to generate a localized data map. The localized data provides a user with a visual representation of a specific parameter or parameters measured within the work area traversed.

In some embodiments, the localized data map is used to determine indoor or outdoor demands, such as irrigation, fertilization, weed control, weed removal, ice removal, snow removal, debris removal, dust or gravel removal, or a combination thereof. For example, the localized data map can be used to determine the location of the presence of ice, and subsequently be used to apply various deicing methods or treatments for removal.

While embodiments of the disclosed system and method have been described, it should be understood that the disclosed system and method are not so limited and modifications may be made without departing from the disclosed system and method. The scope of the disclosed system and method are defined by the appended claims, and all devices, processes, and methods that come within the meaning of the claims, either literally or by equivalence, are intended to be embraced therein.

The invention claimed is:

1. A method for generating a localized turf grass data map and for placement of a moveable lighting apparatus, the method comprising:
   (a) traversing an area of turf grass with an outdoor power equipment machine, the outdoor power equipment machine including at least one sensor, wherein the sensor is configured to receive data;
   (b) collecting turf grass data utilizing the sensor;
   (c) communicating the turf grass data to generate a localized turf grass data map, wherein the step of traversing an area and the step of collecting turf grass data are simultaneous;
   (d) creating a light exposure map based on the turf grass data:
   (e) identifying a desired placement area for the moveable lighting apparatus based on the light exposure map; and
   (f) advancing the moveable lighting apparatus to the desired placement area.

2. The method as in claim 1, wherein the turf grass data is obtained by the at least one sensor operatively connected to (i) a mower blade associated with the outdoor power equipment machine, (ii) an axle of the outdoor power equipment machine, or (iii) a motor associated with the outdoor power equipment machine.

3. The method as in claim 1, wherein the step of communicating turf grass data is concurrent with or subsequent to the step of collecting turf grass data.

4. The method as in claim 1, wherein the turf grass data is associated with a measurement of at least one of (i) resistance, (ii) load, (iii) axle torque, or a combination thereof.

5. The method as in claim 1, wherein the turf grass data is associated with a measurement of at least one of (i) light, (ii) moisture content, (iii) temperature, (iv) weed presence, (v) grain, or (vi) soil compaction.

6. The method as in claim 1, wherein the turf grass data map characterizes areas of high turf grass density and low turf grass density.

7. The method as in claim 1, wherein the turf grass data map is used to determine at least one turf grass demand, and wherein the turf grass demand comprises irrigation, fertilization, aeration, light, weed control, weed removal, grooming, brushing, or a combination thereof.

8. A method, comprising:
receiving, at a computing system from an outdoor power equipment machine, turf grass sensor data indicative of localized turf grass characteristics in a work area;
storing the turf grass sensor data in a memory associated with the computing system;
receiving, at the computing system from the outdoor power equipment machine, sensor data indicative of a history of geographic locations of the outdoor power equipment machine within the work area;
storing the historical geographic location sensor data in a memory associated with the computing system;
accessing, from the memory, the turf grass sensor data and the historical geographic location sensor data;
correlating the turf grass sensor data and the historical geographic location sensor data to form aligned sensor data;
generating a localized turf grass data map based on the aligned sensor data;
creating a light exposure map based on the turf grass data;
identifying a desired placement area for a moveable lighting apparatus based on the light exposure map; and
advancing the moveable lighting apparatus to the desired placement area.

9. The method as in claim 8, wherein correlating the turf grass sensor data and the historical geographic location sensor data comprises aligning at least one timestamp associated with the turf grass sensor data with at least one timestamp associated with the historical geographic location sensor data.

10. The method as in claim 8, comprising:
identifying areas of turf grass requiring treatment within the work area based on the localized turf grass data map; and
applying a treatment to the areas of turf grass in the work area.

11. The method as in claim 10, wherein the treatment comprises providing an artificial light source, irrigation, fertilization, aeration, insect control, weed control, weed removal, grass seed, grooming, brushing, or a combination thereof.

12. The method as in claim 8, comprising:
identifying areas of high turf grass density within the work area based on the localized turf grass data map; and
scheduling a mowing operation directed to the areas of high turf grass density in the work area.

* * * * *